US00PP12728P2

(12) United States Plant Patent
van Geest

(10) Patent No.: US PP12,728 P2
(45) Date of Patent: Jun. 25, 2002

(54) FICUS PLANT NAMED 'MINI MIDNIGHT'

(75) Inventor: Jan van Geest, S'Gravenzande (NL)

(73) Assignee: Plantenwekerij J. Van Geest, B.V., JP S'Gravenzande (NL)

( * ) Notice: Subject to any disclaimer, the term of this patent is extended or adjusted under 35 U.S.C. 154(b) by 0 days.

(21) Appl. No.: 09/661,158

(22) Filed: Sep. 13, 2000

(51) Int. Cl.[7] ..... A01H 5/00

(52) U.S. Cl. ..... Plt./211

(58) Field of Search ..... Plt./211

*Primary Examiner*—Bruce R. Campell
*Assistant Examiner*—Susan B. McCormick
(74) *Attorney, Agent, or Firm*—Foley & Lardner

(57) ABSTRACT

A new and distinct cultivar of *Ficus benjamina* particularly characterized by dark green foliage with a very compact growth habit, small leaves and a heavily branching, and upright growth habit.

2 Drawing Sheets

BACKGROUND OF THE INVENTION

The present invention relates to a new and distinct cultivar of *Ficus benjamina* 'Midnight'. The varietal denomination of the new cultivar is 'Mini Midnight'. The new variety was discovered as a mutation in a controlled planting of *Ficus benjamina* 'Midnight' in a greenhouse in _s'Gravenzande, The Netherlands in 01/05 in 1996.

SUMMARY OF THE INVENTION

The new variety is a mutation of the variety *Ficus 'Midnight'* U.S. Plant Pat. No. 9,856. The new variety was selected by The Discovery of a mutation and selected by Jan van Geest. The Ficus 'Midnight' Plants that the new variety mutated from were in a controlled planting under glass in Gravenzade, The Netherlands at The Kwekerij P. van Geest in Jan. 5, 1996. The new variety was first asexually propagated by vegetative cutting in February 1996, in 's'Gravenzande, The Netherlands. Asexual reproduction through succeeding generations has established that the combination of characteristics as herein disclosed for the new cultivar are firmly fixed and retained through successive generations of asexual reproduction.

COMPARISON WITH PARENT AND OTHER VARIETIES

Comparison of the Ficus 'Mini Midnight' differs from the parent plant the Ficus 'Midnight' in that the size of the leaves are much smaller and the plant has a heavy lateral branching than that of the parent plant. The growth pattern is much more compact and the internodes are of much shorter length. Midnight grown under the same conditions of the 'Mini Midnight' will have larger leaves, sparser branching and internode lengths will be longer. The leaf color of the Midnight and the 'Mini Midnight' are nearly identical when grown under identical conditions. The leaves of both 'Midnight' and 'Mini Midnight' are thick glossy and leathery and a dark attractive green that is almost blue-black without variegation on the leaves.

BRIEF DESCRIPTION OF THE DRAWINGS

The accompanying photographic illustrations show a specimen of the new cultivar as true to color as is reasonably possible to make an illustration of this character with one illustration showing the growth habit and the other illustration showing the foliage. Phenotypic expression may vary depending on light, environmental and cultural conditions.

Sheet 1 is a side view of the plant.

Sheet 2 is a close up of the leaves of the new variety.

DETAILED DESCRIPTION OF THE NEW VARIETY

'Mini Midnight' has not been observed under all possible environmental conditions. The phenotypic expression may vary with variations in environment such as temperature, light intensity, day length and cultural conditions, without a change in the genotype of the plant.

The following observations and descriptions are of an 8 month old plant grown in A shade house covered with Saran providing 73% shade in Homestead, Fla., USA during the months of January through July of 2000. In this description, color references are to The Royal Horticultural Society Color Chart (R.H.S.C.C.). The color references are as approximate as possible as color depends to a degree on horticultural practices such as light level and fertilization rates.

The terminology used in the color descriptions refers to plate numbers in this color chart.

Botanical: *Ficus benjamina* 'Mini Midnight'.
Parentage: Mutation of *Ficus benjamina* 'Midnight'.
Propagation: By vegetative cuttings and other known asexual reproduction techniques.

Plant

Form: Very compact, very upright, upwardly branching, ascending regularly and richly branching.

*Growth*.—a. Lateral branches tend to be at 30 to 45 degrees to the trunk, but slightly weeping at the top. b. Height Attained: 1 meter. c. Plant Spread: Approximately 60 cm. d. Trunk Diameter: 7 mm, as measured 8 cm above the soil line.

*Foiliage*.—a. Size about 1.5 cm wide by 4 cm long (to leaf tip). b. Quantity Multiple, Numerous. c. Color New foliage: upper side — near 137B; Underside — near 137B. Old foliage: Upper side — near 131A; Underside — near 139A to 139B. d. Shape Ovate with acuminate leaf tip slightly coarsely sinuate and glabrous. e. Texture — Smooth, leathery, glossy, underside smooth, matte. f. Veination — Single mid-rib vein running from petiole to leaf tip, convex on underside, light green near 145D. g. Edge — Smooth, slightly undulated. h. Serration — None. i. Stipules — The cap-like stipules enclose the young bud of the emerging leaf a the base of the petiole, abscising and falling away as the leaf begins to form a petiole. j. Auricle — Absent. k. Petiole — Green, RHS 138A; about 10 mm long; 1 mm diameter. l. Disease Resistance — No particular claim is made to disease resistance. m. Rachis — None.

*Wood*.—a. New Shoots — Color — near 197B; smooth. b. Old Wood — Color near 199A. To date and under conditions described herein, the new variety has not borne flowers or fruit. c. Node Spacing — About 7 to 15 mm. d. Preferred Growing Conditions — 20 degrees C. to 32 degrees C. e. Reproductive Organs — Not observed. f. Temperature range — From 2 degrees C. to 40 degrees C with optimal growth occurring between 26 degrees C. to 35 degrees C.

I claim:

1. A new and distinct plant as herein described and illustrated.

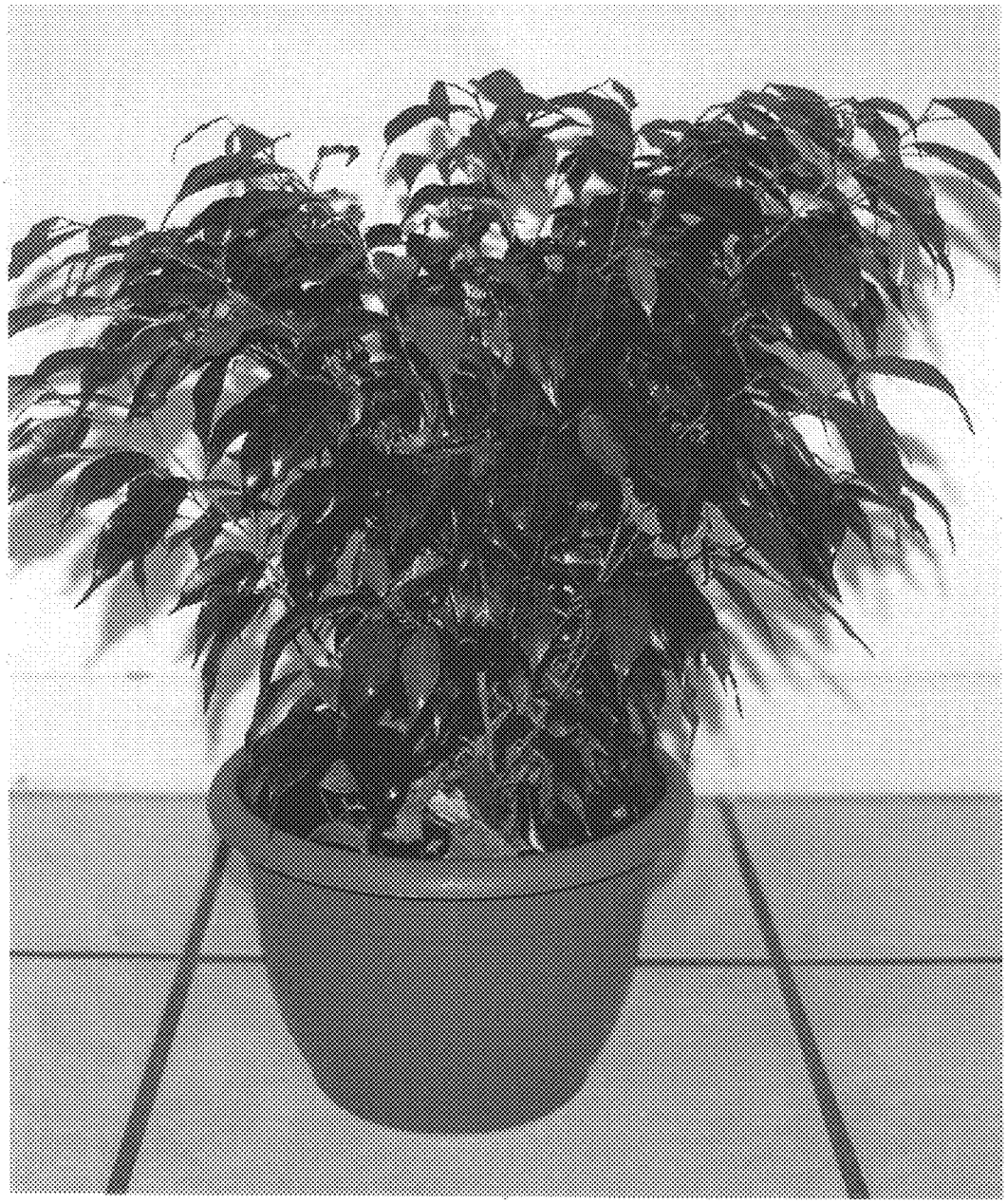

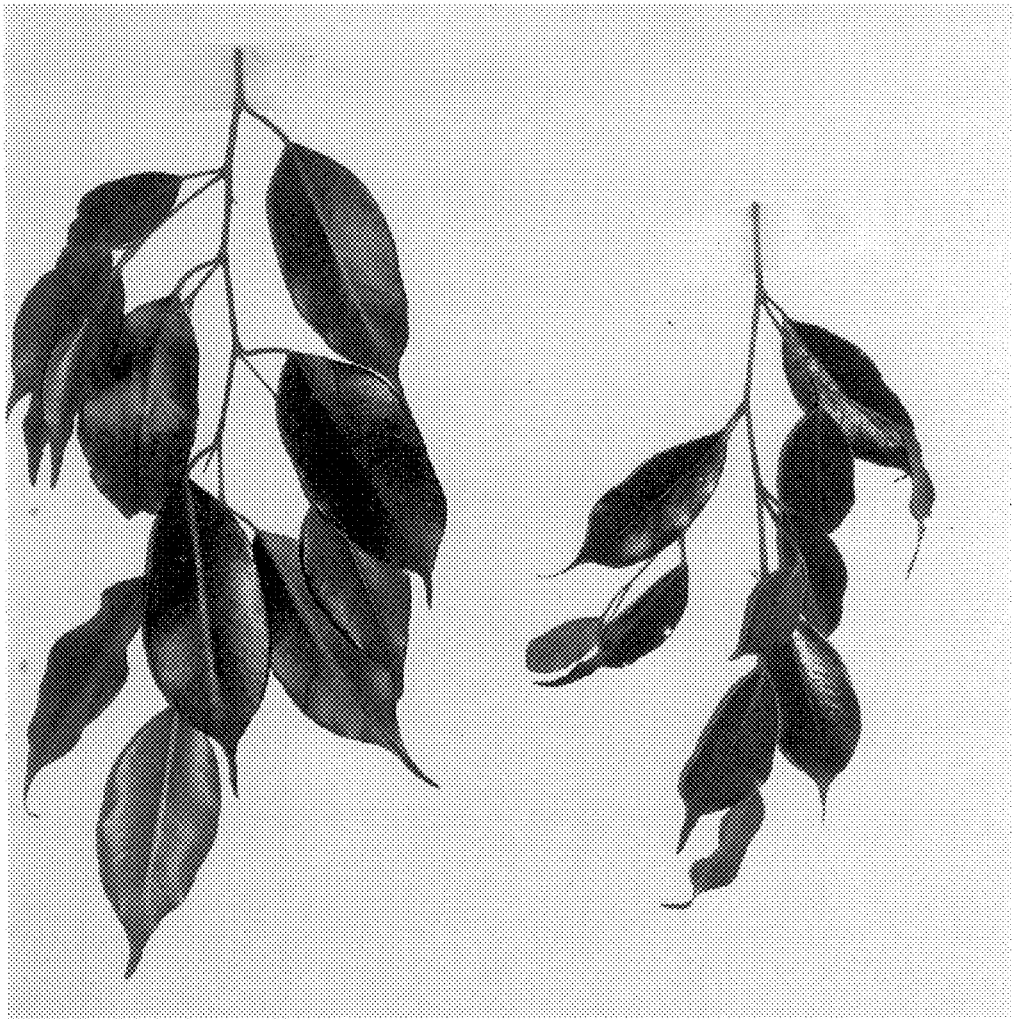

* * * * *